United States Patent [19]

Blank et al.

[11] Patent Number: 5,367,108
[45] Date of Patent: Nov. 22, 1994

[54] PROCESS FOR THE PREPARATION OF DINITRO-POLYALKYLBENZENES

[75] Inventors: Heinz-Ulrich Blank, Odenthal-Gloebusch; Bernd-Michael König, Duesseldorf, both of Germany

[73] Assignee: Bayer Aktiengesellschaft, Leverkusen, Germany

[21] Appl. No.: 80,026

[22] Filed: Jun. 18, 1993

[30] Foreign Application Priority Data

Jun. 24, 1992 [DE] Germany ................ 4220565

[51] Int. Cl.⁵ ............................ C07C 205/06
[52] U.S. Cl. .......................... 568/932; 568/933
[58] Field of Search .................. 568/932, 933

[56] References Cited

U.S. PATENT DOCUMENTS 1,892,128 12/1932 Barbier .
2,864,871 12/1958 Morningstar .
3,153,099 10/1964 Lind .
4,136,117 1/1979 Diehl et al. .

FOREIGN PATENT DOCUMENTS 679279 8/1939 Germany .
1105860 12/1959 Germany .
3317649 11/1984 Germany .

OTHER PUBLICATIONS

Houben–Weyl "Methoden Der Organischen Chemie", 1971, Georg Thieme Verlag, Stuttgart.
The Journal of the American Chemical Society, Jul.–Dec. 1943, E. Newton, "Polyisopropyl–benezens. II. Nitro and Amino Derivatives" vol. 65, pp. 2434–2439.
Chem. Abstracts vol. 102:62669h (1985).
Chem. Abstracts, vol. 56:11497 (1962).

*Primary Examiner*—Johann Richter
*Assistant Examiner*—John D. Peabody
*Attorney, Agent, or Firm*—Sprung Horn Kramer & Woods

[57] ABSTRACT

Dinitro-polyalkylbenzenes can be prepared by nitration of polyalkylbenzenes using $HNO_3$ in the presence of $H_2SO_4$ in such a manner that at least 50% of the $H_2SO_4$ is present as reaction medium and $HNO_3$ and the polyalkylbenzene and any remaining $H_2SO_4$ are added simultaneously in such a manner that the added substances polyalkylbenzene and $HNO_3$ are in the molar ratio of 1:2–10. $H_2SO_4$ is used at a concentration from 81 to 96% by weight and $HNO_3$ at a concentration from 95 to 100% by weight. For the work-up, the dinitro-polyalkylbenzenes are first freed from the majority of the acids and then treated with a highly dilute aqueous solution of a dispersant for separating off residual acid.

19 Claims, No Drawings

PROCESS FOR THE PREPARATION OF DINITRO-POLYALKYLBENZENES

BACKGROUND OF THE INVENTION

1. Field of the Invention

The present invention relates to a process for the dinitration of polyalkylbenzenes. Nitration is carried out in this case in a reaction medium of $H_2SO_4$ with $HNO_3$. No organic solvent is required for this process.

An important representative of dinitro-polyalkylbenzenes is 2,4-dinitro-1,3,5-triisopropylbenzene, which acts as an important precursor in plastics chemistry.

2. Description of the Related Art 1,3,5-triisopropylbenzene can be mononitrated in a simple manner in the system $HNO_3$/acetic anhydride; in a likewise facile reaction, 2,4,6-trinitro-1,3,5-triisopropylbenzene is obtained by addition of 1,3,5-triisopropylbenzene to a $H_2SO_4/HNO_3$ mixture (J. Am. Chem. Soc. 65 (1943), 2434). A dinitro-triisopropylbenzene cannot be prepared by the process variants described. Other polyalkylbenzenes, such as 1,3-diisopropylbenzene, 1,4-diisopropylbenzene, 1,3-dimethyl-5-tert-butylbenzene and 1,3-dimethyl-5-dimethylpropylbenzene, can be nitrated by introducing each particular starting material together with concentrated sulphuric acid and adding concentrated $HNO_3$ (J. Am. Chem. Soc., loc.cit.; German Offenlegungsschrift 3 317 649). In the case of dinitration, unsatisfactory results are obtained in this case.

The methods described are therefore suitable for the mononitration of polyalkylbenzenes. The trinitration mentioned of 1,3,5-triisopropylbenzene only succeeded as a result of high temperature elevation to approximately 100° C., where the nitrated starting material melted and in the course of further nitration became a pasty mass. The yields achievable in the manner described and, particularly, the purities achievable are unsatisfactory. This must generally be assigned to the circumstances that a dinitro or trinitro product obtained in the further nitration encloses still unreacted mononitro product and thus prevents its further nitration.

Attempts have therefore already been made to carry out the nitration, for example of 1,3,5-triisopropylbenzene, in the two-phase system liquid/liquid (starting material in the organic solvent/acids) instead of in the two-phase system solid/liquid (mononitro-triisopropylbenzene/acids). Suitable solvents which have been described for this purpose are aliphatic hydrocarbons (mixtures having a boiling point range from 170° to 190° C.) (German Patent Specification 11 05 860). Such a procedure is always associated with the necessity for a solvent circulation and handling thereof; in addition, aspects relating to health at work and safety (fire hazard) must be taken into account.

SUMMARY OF THE INVENTION

It has now been shown that a highly selective dinitration of polyalkylbenzenes is possible if only $H_2SO_4$ is employed as the reaction medium without the use of an organic solvent and the starting material and the $HNO_3$ are simultaneously fed into this medium, the parameters given below being adhered to.

A process has been found for the preparation of dinitropolyalkylbenzenes of the formula

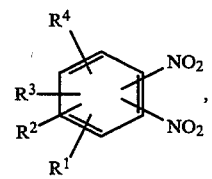

in which $R^1$ and $R^2$, independently of each other, denote straight-chain or branched $C_1$–$C_8$-alkyl, $R^3$ represents hydrogen, straight-chain or branched $C_1$–$C_4$-alkyl and $R^4$ denotes hydrogen, straight-chain or branched $C_1$–$C_4$-alkyl, chlorine or bromine, where, in the absence of chlorine or bromine, the total number of the alkyl C atoms is at least 4, by nitration of polyalkylbenzenes of the formula

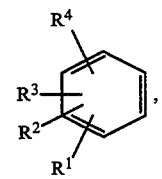

in which $R^1$ to $R^4$ have the meaning given, a solid being produced during the reaction, using $HNO_3$ in the presence of $H_2SO_4$, which is characterised in that a) $H_2SO_4$ is introduced as reaction medium, without the accompanying use of an organic solvent, in an amount from 180 to 1000 g, preferably 200 to 500 g, particularly preferably 250 to 350 g per mole of polyalkylbenzene and at a concentration from 81 to 96% by weight, preferably 85 to 94% by weight, particularly preferably 89 to 93% by weight, at at least 30%, preferably at at least 50%, of the $H_2SO_4$ amount, b) the polyalkylbenzene, 95 to 100% strength by weight $HNO_3$ and any remaining $H_2SO_4$ are fed simultaneously in the range from 0° to 60° C., preferably 15° to 40° C., particularly preferably 20° to 35° C., in such a manner that the added substances polyalkylbenzene and $HNO_3$, during the addition, are in the molar ratio of 1:2–10, preferably 1:2.5–5, particularly preferably 1:2.7–3.5, c) after the addition, the reaction mixture is kept at 10° to 70° C., preferably 30° to 60° C., particularly preferably 40° to 55° C., for further reaction and d) the dinitro-polyalkylbenzene is obtained by work-up.

DETAILED DESCRIPTION OF THE INVENTION

Straight-chain or branched $C_1$–$C_8$-alkyl is, for example, methyl, ethyl, propyl, isopropyl, butyl, isobutyl, tert-butyl and the straight-chain and branched pentyls, hexyls, heptyls and octyls.

In the polyalkylbenzenes to be used according to the invention, the total number of C atoms in the alkyl chains is at least 4, preferably at least 6.

Polyalkylbenzenes which can be used according to the invention are preferably those of the formula

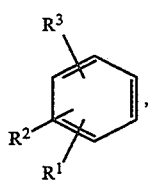

(III)

in which $R^1$, $R^2$ and $R^3$ have the meaning given above.

Polyalkylbenzenes which can be used according to the invention are particularly preferably those of the formula

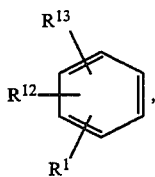

(IV)

in which $R^1$ has the above range of meanings and $R^{12}$ and $R^{13}$, independently of each other, denote straight-chain or branched $C_1$-$C_4$-alkyl.

Important polyalkylbenzenes for the process according to the invention are: 1,3,5-triisopropylbenzene, 1,2,4-triisopropylbenzene, 1,3-diisopropylbenzene, 1,3-diisopropyl-5-methylbenzene, 1,3,5-tri-t-butylbenzene, 1,2,4,5-tetraisopropylbenzene and 1,2-dimethyl-4-chlorobenzene.

The reaction medium $H_2SO_4$ in the amount described and at the concentration described is introduced at at least 50% of its total amount. The remainder of the $H_2SO_4$ is added in such a case together with the $HNO_3$. To simplify the overall addition programme, all of the $H_2SO_4$ is preferably introduced as the reaction medium.

The process according to the invention is principally characterised by the simultaneous addition of the polyalkylbenzene and the $HNO_3$. These two reactants, during the addition, have the molar ratio given above.

During the addition, the reaction mixture is kept at a temperature in the range from 0° to 60° C., preferably 15° to 40° C., particularly preferably 20° to 35° C. Cooling is generally required for this because of the highly exothermic reaction. However, it is possible to allow the temperature of the reaction mixture to rise during the addition from a value in the lower part of the range given to a value in the upper part of the range given and thus to decrease the amount of cooling used for the reaction mixture. After the addition, the reaction mixture is subjected to further reaction which takes place at a temperature of a higher order than the addition. The temperature range of this further reaction is generally 10° to 70° C., preferably 30° to 60° C., particularly preferably 40° to 55° C. The rise in temperature described during the addition makes it possible to pass directly from the temperature of addition to the temperature of the further reaction. The time duration of the further reaction is dependent on the size of the batch and on the progress of the reaction in a manner known to those skilled in the art; it can be monitored by simple analytical testing of samples taken and is terminated when no more conversion takes place. The time period for the further reaction is obviously shorter if the addition time period was increased. The overall time for the addition and further reaction will generally not be less than 3 hours even for small batches and generally not exceed 12 hours even for large batches. For a reaction batch of 5 kg total mass of medium and reactants, an addition time of 3 hours and a further reaction time of likewise 3 hours may be mentioned as an example.

The water released in the reaction reduces the concentration of the $H_2SO_4$ used; in this examination, the $HNO_3$ likewise present is not taken into consideration. The $H_2SO_4$ used has a concentration from 81 to 96% by weight (remainder water), preferably 85 to 94% by weight, particularly preferably 89 to 93% by weight and is used in an amount of 180 to 1000 g, preferably 200 to 500 g, particularly preferably 250 to 350 g per mole of the polyalkylbenzene. These figures for concentration and amounts are intended for the accompanying use of a 95 to 100% strength by weight $HNO_3$, preferably a 98 to 100% strength by weight $HNO_3$. Obviously, by means of a simple calculation, a somewhat higher water content in the $HNO_3$ can be compensated by a somewhat higher $H_2SO_4$ concentration in the context of the abovementioned ranges.

After termination of the reaction, the $H_2SO_4$ in the reaction mixture preferably has a concentration of 75 to 85% by weight, preferably 77 to 84% by weight, particularly preferably 79 to 83% by weight, which is based only on the total weight of the $H_2SO_4$ and the dilution water of this $H_2SO_4$ used and the additional water formed by the reaction and does not take into account the amount of the $HNO_3$ likewise present.

In the process according to the invention a solid is produced during the reaction. This can be the dinitro end product, but in many cases is the mononitro intermediate. The successful performance of the dinitration is surprising, since it had to be feared that still unreacted material would be covered by the formation of the solid and thus excluded from the reaction.

Following the further reaction period, the dinitropolyalkylbenzene present in solid form is separated from the majority of the acids ($H_2SO_4$+$HNO_3$), for example by filtration or centrifugation. However, the remaining solid product still contains adhering and enclosed residual acids. To remove them and to give a required increase in purity, depending on purity requirements, further work-up can subsequently be carried out by recrystallisation from solution or from the melt, by extraction or by slurrying in water. For the slurrying in water, a small amount of alkali metal hydroxide or alkali metal carbonate can additionally be used. In a particularly elegant manner, slurrying in water is performed with good mixing, 0.01 to 1% by weight, preferably 0.05 to 0.5% by weight, particularly preferably 0.05 to 0.1% by weight, of dispersant being added to the water. As a result of this treatment, even residues of enclosed acids are effectively removed. Obviously, higher proportions of dispersant are also possible; however, they do not bring any additional success but rather impair the purity of the worked-up product and increase the difficulty of disposal of such a treatment water. The type of the dispersant is not critical; all cationic, anionic or nonionic dispersants known to those skilled in the art have proved to be suitable.

The criterion applied to this variant of the work-up is therefore principally the price of the dispersant. From this aspect, ethoxylates and propoxylates of fatty alcohols, fatty acids and fatty acid derivatives, and particularly alkanesulphonates and alkylbenzenesulphonates have proved to be expedient.

The yield of dinitro-polyalkylbenzene reaches at least 90% of the theoretical yield, in many cases 95% and above. As a typical yield for the 2,4-dinitro-1,3,5-triisopropylbenzene, 98% of the theoretical yield may be cited, where such a material contains 98.5% of 2,4-dinitro-1,3,5-triisopropylbenzene, 0.4 to 0.5% of 2-nitro-1,3,5-triisopropylbenzene, 0.3 to 0.4% of 2,4,6-trinitro-1,3,5-triisopropylbenzene and less than 0.1% of acids. The process according to the invention has a series of advantages compared to the previous processes:

- the complex procedure with a solvent is dispensed with; the space yield is considerably increased by this means.
- the simultaneous addition of starting material and $HNO_3$ gives a highly selective reaction.
- as a result of the preferred variant of the work-up using dispersant-containing water, the use of a solvent for any recrystallisation or extraction is also dispensed with and thus supplements the omission of a solvent during the reaction.
- the highly effective treatment of the product with dispersant-containing water permits a reduction of the waste water pollution.
- the removal of the acids prior to the secondary treatment with dispersant-containing water allows these acids to be produced in a concentration suitable for the conventional $H_2SO_4$ work-up process, so that, in this case, both the majority of the $HNO_3$ and also all of the $H_2SO_4$ can be returned into the process.

EXAMPLE 1292.1 g of 91% strength $H_2SO_4$ (=1175.8 g of 100% strength=12 mol) were introduced into a 4 l sulphation vessel having a bottom outlet and anchor agitator. To this initially introduced amount were fed simultaneously in the course of 3 hours 834.1 g of 98% pure triisopropylbenzene (=817.3 g of 100% pure=4 mol) and 771.6 g of 98% strength $HNO_3$ (=756.2 g of 100% pure=12 mol). The temperature in this case was kept at 25° C. (maximum rise to 30° C.) by external cooling. After about 2 minutes, solid product began to precipitate out. In the course of the addition, the suspension became temporarily thicker, but remained stirrable without problems. Encrustations and lump formation did not occur. Towards the end of the addition, the particle size of the suspended product became smaller again. Following completion of the addition, the reaction mixture was heated in the course of 30 minutes to 50° C., where only a slight development of nitrous gases occurred; the mixture was stirred for a further 3 hours at 50° C.

Work-Up Variant 1

The fine, highly mobile suspension was discharged into about 2000 ml of ice/water mixture (1:1) in the course of 30 seconds. The water-diluted reaction mixture was stirred for 30 minutes and then filtered using suction within about 50 seconds. The crude product obtained from this (1512 g having an acid content of 9.2% by weight by titration) was stirred with 1510 ml of a 0.075% strength by weight aqueous solution of sodium alkylbenzenesulphonate for 1.5 to 2 h at room temperature, then filtered using suction and washed three times, each time using 750 ml of water, and air-dried. The moist weight was about 1290 g, the dry weight 1172 g (=98% of the theoretical yield). The dry product constituted almost colourless crystals having a melting point from 135° to 135.5° C. Gas-chromatographic analysis gave a content of 98.6% of dinitro-triisopropylbenzene, 0.4 to 0.5% of nitro-triisopropylbenzene, 0.3 to 0.4% of trinitro-triisopropylbenzene, 0.06% of water and 0.08% of residual acid (all as % by weight). Unreacted triisopropylbenzene could not be detected.

Work-Up Variant 2

The reaction mixture was discharged from the sulphation vessel onto a glass frit and filtered using suction. 1134 g of used acid were obtained having a content of about 69% by weight of $H_2SO_4$ and about 14.5% by weight of $HNO_3$ (the remainder of about 16.5% is water; the content of $H_2SO_4$ and $H_2O$ corresponds to an 81% strength $H_2SO_4$). The filter cake remaining on the glass frit was washed using about 1000 ml of water, 1090 g of wash water resulting, having an acid content of 15.5% by weight, calculated as $H_2SO_4$. The crude product (1520 g) was stirred with 1520 ml of a 0.1% strength by weight aqueous solution of sodium alkylbenzenesulphonate for about 2 h at room temperature, filtered using suction, washed 4 times, each time using 750 ml of water, and air-dried. The dried product obtained was 1178 g of almost colourless crystals (=98% of the theoretical yield) having a melting point of 135° to 135.5° C. The gas-chromatographic analysis gave a content of 98.8% of dinitro-triisopropylbenzene, 0.5% of nitro-triisopropylbenzene, 0.3% of trinitro-triisopropylbenzene, 0.03% of $H_2O$ and 0.02% of residual acids (all in % by weight). Unreacted triisopropylbenzene could not be detected.

What is claimed is:

1. A process for the preparation of a dinitro-polyalkylbenze of the formula

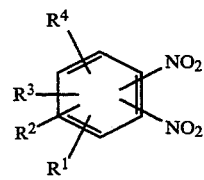

in which
$R^1$ and $R^2$, independently of each other, denote straight-chain or branched $C_1-C_8$-alkyl,
$R^3$ represents hydrogen, straight-chain or branched $C_1-C_4$-alkyl and
$R^4$ denotes hydrogen, straight-chain or branched $C_1-C_4$-alkyl chlorine or bromine,
where, in the absence of chlorine or bromine, the total number of the alkyl C atoms is at least 4, by nitration of a polyalkylbenzene of the formula

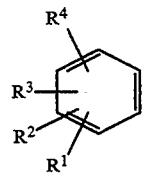

in which $R^1$ to $R^4$ have the meanings given, a solid being produced during the reaction, using $HNO_3$ in the presence of $H_2SO_4$, wherein
a) sulphuric acid of 81 to 96% by weight strength is introduced as reaction medium, without the accompanying use of an organic solvent, in an amount of from 180 to 1000 g per mole of polyalkylbenzene; at least 30% of the sulphuric acid amount being introduced prior to the introduction of any reactants, b) the polyalkylbenzene, 95 to 100% strength by weight HNO$_3$ and any remaining sulphuric acid are fed simultaneously in the range of from 0° to 60° C., in such manner that the added substances polyalkylbenzene and HNO$_3$, during addition, are in the molar ratio of 1:2–10, c) after the addition, the reaction mixture is kept at 10 to 70° C. for further reaction and d) the dinitro-polyalkylbenzene is separated from the reaction mixture.

2. The process of claim 1, wherein sulphuric acid is used as the reaction medium in an amount of from 200 to 500 g per mole of polyalkylbenzene.

3. The process of claim 1, wherein the sulphuric acid strength is from 85 to 94% by weight.

4. The process of claim 3, wherein the sulphuric acid strength is 89 to 93% by weight.

5. The process of claim 1, wherein the polyalkylbenzene, the HNO$_3$ and any remaining sulphuric acid are fed in the range of 15 to 40° C.

6. The process of claim 1, wherein polyalkylbenzene and HNO$_3$ are in the molar ratio of 1:2.5–5.

7. The process of claim 6, wherein polyalkylbenzene and HNO$_3$ are in the molar ratio of 1:2.7–3.5.

8. The process of claim 1, wherein, after the reaction, the reaction mixture is kept at 30° to 60° C.

9. The process of claim 1, wherein a polyalkylbenzene of the formula

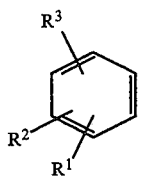

is used, in which $R^1$ and $R^2$, independently of each other, denote straight-chain or branched $C_1$–$C_8$-alkyl and $R^3$ represents hydrogen or straight-chain or branched $C_1$–$C_4$-alkyl.

10. The process of claim 9, wherein a polyalkylbenzene of the formula

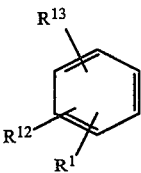

is used, in which $R^1$ denotes straight-chain or branched $C_1$–$C_8$-alkyl and $R^{12}$ $R^{13}$, independently of each other, denote straight-chain or branched $C_1$–$C_4$-alkyl.

11. The process of claim 1, wherein a polyalkylbenzene having at least 6 alkyl C atoms is used.

12. The process of claim 1, wherein all of the sulphuric acid is initially introduced.

13. The process of claim 1, wherein the reaction is carried out in such a manner that the H$_2$SO$_4$, after the reaction is terminated, makes up 75 to 85% by weight of the total weight of H$_2$SO$_4$ and dilution water and water formed in the reaction.

14. The process of claim 13, wherein the reaction is carried out in such a manner that the H$_2$SO$_4$, after the reaction is terminated, makes up 77 to 84% by weight of the total weight of H$_2$SO$_4$ and dilution water and water formed in the reaction.

15. The process of claim 14, wherein the reaction is carried out in such a manner that the H$_2$SO$_4$, after the reaction is terminated, makes up 79 to 83% by weight of the total weight of H$_2$SO$_4$ and dilution water and water formed in the reaction.

16. The process of claim 1, wherein the crude dinitro-polyalkylbenzene, after removal of the majority or H$_2$SO$_4$ and HNO$_3$, is treated by treatment with a 0.01 to 1% strength by weight aqueous solution of a dispersant with mixing.

17. The process of claim 16, wherein the crude dinitro-polyalkylbenzene, after removal of the majority of H$_2$SO$_4$ and HNO$_3$, is treated by treatment with a 0.05 to 0.5% strength by weight aqueous solution of a dispersant with mixing.

18. The process of claim 17, wherein the crude dinitro-polyalkylbenzene, after removal of the majority of H$_2$SO$_4$ and HNO$_3$, is treated by treatment with a 0.05 to 0.1% strength by weight aqueous solution of a dispersant with mixing.

19. The process of claim 1, wherein dinitro-triisopropylbenzenes are prepared by reaction of triisopropylbenzenes.

* * * * *

UNITED STATES PATENT AND TRADEMARK OFFICE
CERTIFICATE OF CORRECTION

PATENT NO. : 5,367,108
DATED : November 22, 1994
INVENTOR(S) : Blank, et al.

It is certified that error appears in the above-indentified patent and that said Letters Patent is hereby corrected as shown below:

Col. 8, line 35  Delete " or " and substitute -- of --

Signed and Sealed this

Ninth Day of December, 1997

Attest:

BRUCE LEHMAN

Attesting Officer

Commissioner of Patents and Trademarks